US012716881B2

(12) United States Patent
Han et al.

(10) Patent No.: US 12,716,881 B2
(45) Date of Patent: Aug. 25, 2026

(54) CHARACTERISTIC ELEMENT COMBINATION ANOMALY DERIVATIVE METHOD OF DETERMINING OCCURRENCE OF DEEP CONCEALED PLATE-SHAPED ORE BODY OF HYDROTHERMAL DEPOSIT

(71) Applicant: Kunming University of Science and Technology, Kunming City (CN)

(72) Inventors: Runsheng Han, Kunming City (CN); Yan Zhang, Kunming City (CN); Wenyao Li, Kunming City (CN); Qing Chen, Kunming City (CN)

(73) Assignee: Kunming University of Science and Technology, Kunming City (CN)

( * ) Notice: Subject to any disclaimer, the term of this patent is extended or adjusted under 35 U.S.C. 154(b) by 0 days.

(21) Appl. No.: 18/965,578

(22) Filed: Dec. 2, 2024

(65) Prior Publication Data

US 2025/0347675 A1 Nov. 13, 2025

(30) Foreign Application Priority Data

May 7, 2024 (CN) ........................ 202410551629.9

(51) Int. Cl.
*G01N 33/204* (2019.01)
*G01N 33/24* (2006.01)
*G01V 20/00* (2024.01)

(52) U.S. Cl.
CPC ........... *G01N 33/204* (2019.01); *G01N 33/24* (2013.01); *G01V 20/00* (2024.01)

(58) Field of Classification Search
CPC ....... G01N 33/204; G01N 33/24; G01V 20/00
See application file for complete search history.

(56) References Cited

U.S. PATENT DOCUMENTS

2023/0204810 A1* 6/2023 Zhong ...................... G01V 1/50 702/6

FOREIGN PATENT DOCUMENTS

CN 102487674 A * 6/2012
CN 117289357 A * 12/2023 ............ G01V 11/00
(Continued)

OTHER PUBLICATIONS

Taijin Yu, "Dynamic Monitoring on Settlement and Displacement in the Engineering of Underwater Soft-Base Processing", Geological Exploration for Non-Ferrous Metals, vol. 4, No. 6, Dec. 1995.
(Continued)

*Primary Examiner* — Andrew Schechter
*Assistant Examiner* — Kaleria Knox
(74) *Attorney, Agent, or Firm* — Thomas | Horstemeyer, LLP

(57) ABSTRACT

Provided is a characteristic element combination anomaly derivative method of determining occurrence of a deep concealed plate-shaped ore body of a hydrothermal deposit. The method determines the spatial occurrence of the deep concealed ore body of the hydrothermal deposit through four working procedures, including: fine measurement of a metallogenic structure and systematic collection of samples, sample processing and multi-element quantitative analysis, mathematical model construction of characteristic element combination anomaly, and determination of the occurrence (the strike, the dip direction, the dip angle and the pitch direction) of the deep concealed ore body. The method solves the problem of judging the occurrence of the deep concealed ore body by interpreting geochemical anomalies of a primary halo and a secondary halo.

2 Claims, 14 Drawing Sheets

(56) References Cited

FOREIGN PATENT DOCUMENTS

| | | | | | |
|---|---|---|---|---|---|
| CN | 117784281 A | * | 3/2024 | ............. | G01N 33/24 |
| CN | 118447936 B | | 8/2024 | | |

OTHER PUBLICATIONS

Liang Pan-Feng, "A Geometric Method and Its Application to Determine the Slab Trending of Concealed Ore Body", Mineral Resources and Geology, vol. 28, No. 1, Feb. 2014.
Peyman Afzal, et al., "Application of Concentration-Number and Concentration-Volume Fractal Models to Recognize Mineralized Zones in North Anomaly Iron Ore Deposit, Central Iran", Arch. Min. Sci., vol. 60 (2015), No. 3, p. 777-789.
Peyman Afzal, et al., "Delineation of gold mineralized zones using concentration-volume fractal model in Qolqoleh gold deposit, NW Iran", Ore Geology Reviews, vol. 55, p. 125-133, May 17, 2023.
Sun Jiacong, et al., "Theory and Methods of Ore Field Geomechanics", Science Press, 2016.
First Office Action issued by the State Intellectual Property Office of People's Republic of China in corresponding application No. CN202410551629.9, mailed Oct. 13, 2024.

* cited by examiner

CHARACTERISTIC ELEMENT COMBINATION ANOMALY DERIVATIVE METHOD OF DETERMINING OCCURRENCE OF DEEP CONCEALED PLATE-SHAPED ORE BODY OF HYDROTHERMAL DEPOSIT

CROSS-REFERENCE TO RELATED APPLICATION

This patent application claims the benefit and priority of Chinese Patent Application No. 202410551629.9 filed with the China National Intellectual Property Administration on May 7, 2024, the disclosure of which is incorporated by reference herein in its entirety as part of the present application.

TECHNICAL FIELD

The present disclosure relates to a characteristic element combination anomaly derivative method of determining occurrence of a deep concealed plate-shaped ore body of a hydrothermal deposit, belonging to the field of mineral resources exploration.

BACKGROUND

Determining the occurrence of a deep concealed ore body according to geochemical primary halo or secondary halo anomalies is a frontier research topic of prospecting prediction, and it is also one of the main difficulties in the field of geochemical exploration, which is of great significance to mine production and prospecting. Usually, the occurrence of an ore body is directly controlled by prospecting engineering, and the determining method thereof mainly focuses on the study of the spatial distribution and the occurrence of the exposed ore body. Luo Xuequan (1995) reported a mathematical method of determining occurrence of an ore body. Liang Panfeng (2014) introduced a geometric method of inferring occurrence of a plate-shaped concealed ore body by using geometric principles. Afzal et al. (2013, 2015) used fractal models such as concentration-volume and sediment concentration-quantity to qualitatively infer occurrence of an ore body in combination with a three-dimensional model and a geological model of an ore body. However, a three-dimensional model and an analytical geometry method of an ore body in metal mines are used for location prediction, and the inferred ore body occurrence position thereof often deviates from the actual ore body position due to the limitation of prospecting engineering and spatial extension (depth), spreading and continuity of an ore body.

Based on the progress of geochemical exploration in the past decades, a prospecting method of delineating a deep concealed ore body (deposit) is established by the anomalies of a primary halo or a secondary halo of metal elements in various ore-bearing media based on the diffusion mechanism of metal elements in hydrothermal mineralization, which has made important achievements in prospecting and exploration of different types of metal deposits, and reveals the significance of geochemical exploration in location predicting a deep concealed ore body. However, up to now, there is a lack of universal technical methods to determine the occurrence of a concealed plate-shaped ore body of a hydrothermal deposit. In particular, based on the mathematical model of the distribution of characteristic element combination anomaly, there is no report on the method of characterizing the distribution law of characteristic element combination anomaly of the plate-shaped ore body which is directly controlled by fracture structures and judging the occurrence (the strike, the dip direction, the dip angle and the pitch direction) of the deep concealed ore body.

SUMMARY

The present disclosure provides a characteristic element combination anomaly derivative method of determining occurrence of a deep concealed plate-shaped ore body of a hydrothermal deposit. Based on the fine measurement of metallogenic structures and multi-element quantitative analysis in the working area, the method constructs a mathematical model based on the function of the characteristic element combination anomaly in different cross-sections changing with the spatial position of sampling points and the first-order derivative functions characterizing the occurrence of a deep concealed ore body, so as to judge the occurrence of the concealed plate-shaped ore body of the hydrothermal deposit. It is of great significance to prospect and explore deep and surrounding areas of mines in the new round of prospecting breakthroughs.

The object of the present disclosure is achieved by the following technical solution.

Step 1: fine measurement of a metallogenic structure in the working area and systematic collection of samples The main purpose is to recognize the types of metallogenic structures in the area, systematically identify and collect the samples of faulted rocks that control the mineralization alteration zone.

1. First, the types of metallogenic structures are recognized, where the field geomechanics theory and method (Sun Jiacong, Han Runsheng, 2016) are used to identify the mechanical properties of fractures in different directions that control the mineralization alteration zones in the working area, such as tensile, compressive, torsional and compression-shear fracture structures, through the fine measurement of metallogenic structures in different levels, different veins or cross-sections in the mine area or the exploration working area, and the metallogenic epoch structure and the post-metallogenic structure are distinguished, and the structural geological cross-section diagram is drawn.
2. The samples are systematically collected and identified, where, ore-bearing structures and mineralized alteration points are determined on the surface or in vein tunnels; samples of metallogenic faulted rocks or mineralized altered rocks are collected at a point distance of 5-20 m according to the distribution density of these geological points; intensive sampling is performed at places with strong mineralized alteration, in which the sampling length generally does not exceed 2 m according to the widths of ore-bearing geological bodies; the collected samples are labeled on a structural geological cross-section diagram, and the types of rocks of structural altered rocks are determined with the help of microscopes and X-ray powder diffraction.

Step 2: sample processing and multi-element quantitative analysis

1. Sample processing: in the pollution-free condition, the collected samples are processed and reduced to 200 meshes, and are classified into final samples and accessory samples; wherein the final samples are quantitatively analyzed in the testing institution with national first-class qualification certification, and the accessory samples are used as a backup for inspection or retest;

2. Multi-element quantitative analysis: different testing methods are selected to quantitatively analyze the main metallogenic elements (such as Pb and Zn) in the samples of metallogenic faulted rocks and mineralized altered rocks by using a chemical method. The contents of trace elements related to the mineralization of the deposit are analyzed by using the ICP-MS (Inductively Coupled Plasma Mass Spectrometry) method. The chemical method is used to re-measure the samples whose element content reaches the strong mineralization or ore cut-off grade. Cipher samples or parallel samples are measured according to 3% of the total number of samples to test the accuracy of data. The average error of main elements is less than 5%. The testing method and the instrument precision both meet the analysis requirements. It is checked whether the distribution of element content conforms to a normal or lognormal distribution, and then elements satisfying normal or lognormal distribution are selected.

Step 3: mathematical model construction of multi-element contents and characteristic element combination anomaly.

1. Based on the element content that conforms to the normal or lognormal distribution in a measured cross-section, factor analysis and cluster analysis methods are used to obtain the characteristic element combination indicating deep mineralization information and its anomaly, and a variation law of the characteristic element combination anomaly in the cross-section is analyzed.
2. A mathematical model of metallogenic element content distribution is constructed, where a mathematical model based on a sampling geological point position distance x of different cross-sections as an independent variable and the characteristic element content c, as a function is constructed:

$$c_i = f(x) = a_1 \times \exp\left(-\left((x - b_1 x)/d_1\right)^2\right) \quad (1)$$

where f(x) is the element content in unit of $10^{-6}$; x is the distance in unit of m; $a_1$, $b_1$ and $d_1$ are constants; i is an element; exp is natural exponential function.

The metallogenic element content has the characteristics of the lognormal distribution in the cross-section.

3. mathematical model of the distribution of the characteristic element combination anomaly is constructed: a mathematical model is constructed based on a sampling geological point position x of different cross-sections as an independent variable and the characteristic element combination anomaly $C_j$ as a function;

$$C_j = F(x) = A_1 \times \exp\left(-\left((x - B_1 x)/D_1\right)^2\right) \quad (2)$$

where F(x) is the characteristic element combination anomaly, which is a non-dimensional unit; x is the distance in unit of m; $A_1$, $B_1$ and $D_1$ are constants; j is a characteristic element combination;

Formula (2) reflects the characteristics of the normal distribution of the characteristic element combination j in the cross-section;

The first-order derivative function reflecting the dip direction of the deep concealed ore body is obtained by the first-order derivative of Formula (2):

$$\frac{dC}{dx} = F'(x) = \frac{-2(1 - B_1)^2 x}{D_1^2} \times A_1 \times e^{-((1-B_1)x/D_1)^2} \quad (3)$$

Step 4: determination of the occurrence of the deep concealed plate-shaped blind ore body The first-order derivative function of the characteristic element combination can indicate the occurrence of the deep blind ore body.

(1) determination of the dip direction and the dip angle of the concealed plate-shaped blind ore body if F'(x)<0, it indicates that the dip direction of the concealed plate-shaped blind ore body is consistent with the abnormal divergence direction;

if F'(x)>0, it indicates that the dip direction of the concealed plate-shaped blind ore body is opposite to the abnormal divergence direction;

if F'(x)=(−0.01, 0.01) but ≠0, it indicates that the dip angle of the concealed plate-shaped blind ore body is steep; and if |F'(x)|>0.01, it indicates that the dip angle of the concealed plate-shaped ore body is gentle.

(2) determination of the strike of the deep concealed plate-shaped blind ore body if F'(x)=0 and the deep concealed ore body is distributed linearly, the strike of the deep concealed plate-shaped ore body is consistent with the linear direction.

(3) determination of the pitch direction of the concealed plate-shaped ore body the abnormal drift direction of different elevation planes indicates the pitch direction of the concealed plate-shaped ore body;

if the characteristic element combination anomaly in the deep plane is located to the left of the characteristic element combination anomaly in the shallow plane, it indicates that the concealed plate-shaped ore body is in the pitch direction to the left;

if the characteristic element combination anomaly in the deep plane is located to the right of the characteristic element combination anomaly in the shallow plane, it indicates that the concealed plate-shaped ore body is in the pitch direction to the right;

if the characteristic element combination anomaly in the deep plane and the characteristic element combination anomaly in the shallow plane are in the same position on the planes, it indicates that the concealed plate-shaped ore body is not in the pitch direction.

In one embodiment, a target area is determined based on the determined occurrence of the deep concealed plate-shaped blind ore body, drilling holes are performed in the target area by a drilling rig, and a real occurrence of the deep concealed plate-shaped blind ore body below the target area is determined by ore body obtained from the drilling holes. After determining the real occurrence of the deep concealed plate-shaped blind ore body, ore body mining equipment is used to mine the deep concealed plate-shaped blind ore body under the target area according to the real occurrence.

The scale used refers to the scale of 1:200 to 1:10000.

The level refers to a plane with a certain elevation.

In the method of the present disclosure, a fine measurement of a metallogenic structure and systematic collection of samples in Step 1 and sample processing and multi-element quantitative analysis in Step 2 are the basis of the method, a mathematical model construction of multi-element contents and characteristic element combination anomaly in Step 3 is the key of the method, and determination of the occurrence of the deep concealed plate-shaped blind ore body in Step 4 is the ultimate goal of the method.

The method has the following advantages and technical effects.

(1) The method is suitable for directly determining occurrence of a concealed plate-shaped ore body of a hydrothermal deposit in tunnels or semi exposed-exposed rock areas on the surface.

(2) The method solves the problem that the ore body occurrence position inferred based on a three-dimensional model and an analytic geometry method of an ore body is often deviated from the actual ore body position due to the limitation of prospecting engineering and spatial extension (depth), spreading and continuity of an ore body, and provides a universal method of determining occurrence of a concealed plate-shaped ore body of a hydrothermal deposit.

(3) The method solves the technical bottleneck that it is difficult to determine occurrence of an ore body due to strong abnormal multi-solutions of geophysical prospecting methods.

(4) The method has a wide application range and high accuracy, and can be used to determine occurrence of a deep ore body with the scale of 1:200 to 1:10000.

(5) The method has a clear procedure, strong operability and low working cost.

The present disclosure is not only suitable for magmatic hydrothermal deposits, such as porphyry copper, molybdenum, gold deposits, and metal deposits such as medium-high temperature magmatic hydrothermal tungsten, tin, copper, “four rare” minerals, but also suitable for determining occurrence of a deep ore body in non-magmatic hydrothermal polymetallic deposits, such as structural hydrothermal, metamorphic hydrothermal and other types of copper, lead, zinc, gold, iron, “four rare” minerals and other polymetallic deposits. In addition, for sedimentary metal deposits, only the last three steps can determine occurrence of a deep ore body.

DETAILED DESCRIPTION OF THE EMBODIMENTS

The present disclosure will be further described in detail with the attached drawings and examples, but the scope of protection of the present disclosure is not limited to the above content, and the methods in the embodiments are all conventional methods unless otherwise specified.

Figure 1:
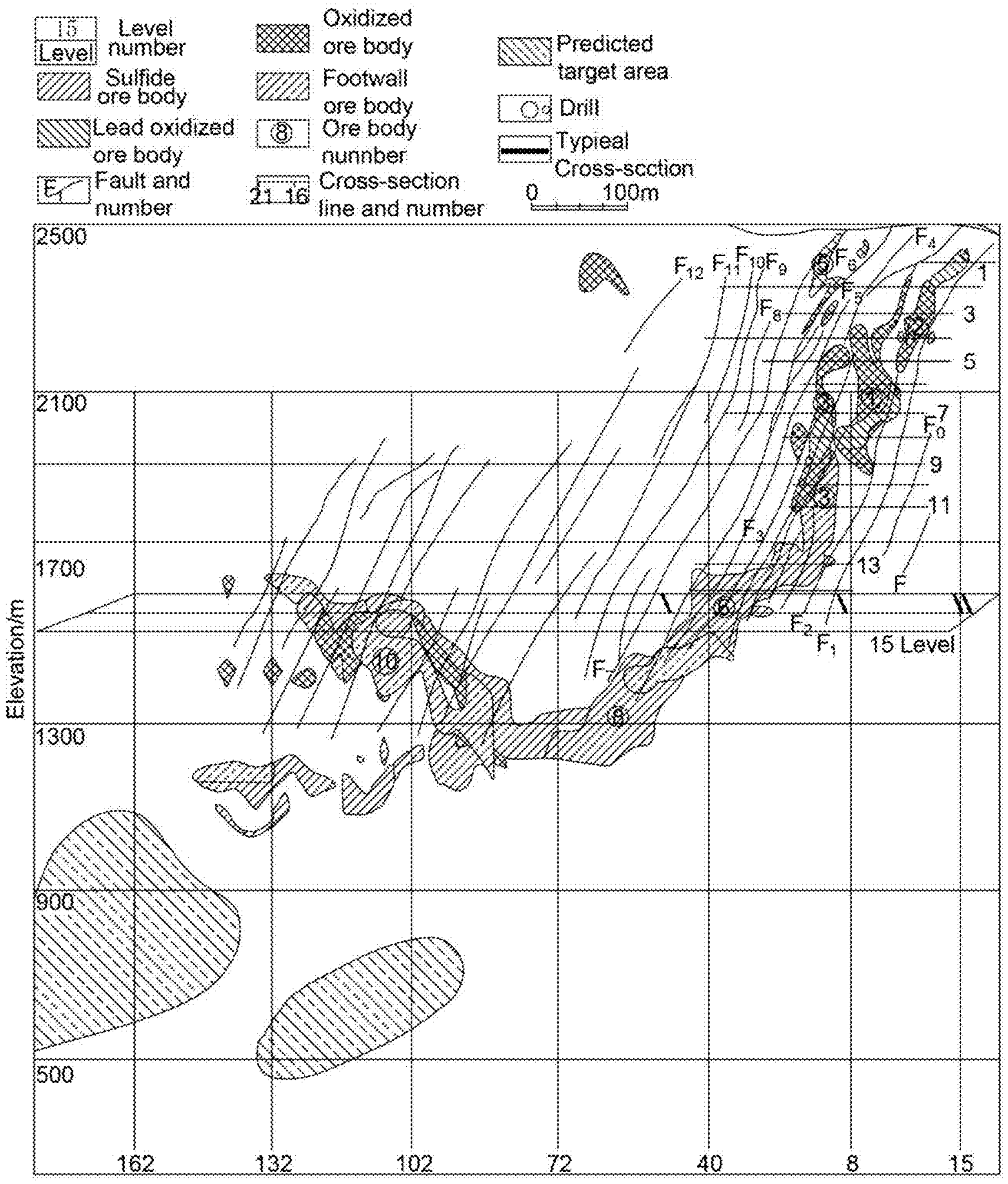
FIG. 1 is a vertical section projection distribution diagram of main ore body of rare metal riched lead-zinc deposit.

Embodiment 1: Determination of Occurrence of a Deep Concealed Plate-Shaped Ore Body in a Lead-Zinc Deposit in Yunnan A germanium-riched lead-zinc deposit is one of the typical hydrothermal deposits in China, which has the characteristics that the grade is high (about 30% Pb+Zn), the reserve volume is large (the deposit and ore body can be up to a large scale), the ore body extends deeply (more than 1600 m), the hydrothermal alteration is strong, and the mineralization alteration combination zone law is obvious. However, the occurrence and the pitch characteristics of the deep ore body change greatly and it is difficult to predict (FIG. 1). Although a geophysical prospecting method such as the TEM(Transient electromagnetic methods) is used, the inference and interpretation of resistivity anomalies obtained by these methods have strong multi-solutions, especially the influence of water-bearing fractures, surface high-voltage lines and underground track facilities in mines, so that it is difficult to distinguish whether the abnormal distribution characteristics indicating the occurrence of the deep ore body are mine-induced anomalies or non-mine-induced anomalies. It is difficult for the interpretation of geochemical anomalies on the surface to determine the occurrence of the deep blind ore body because the concealed ore body is too deep.

The deposit is a hydrothermal lead-zinc deposit obviously controlled by the structure, which lays a foundation for quantitative determination of the occurrence of the deep concealed plate-shaped ore body.

Figure 2:
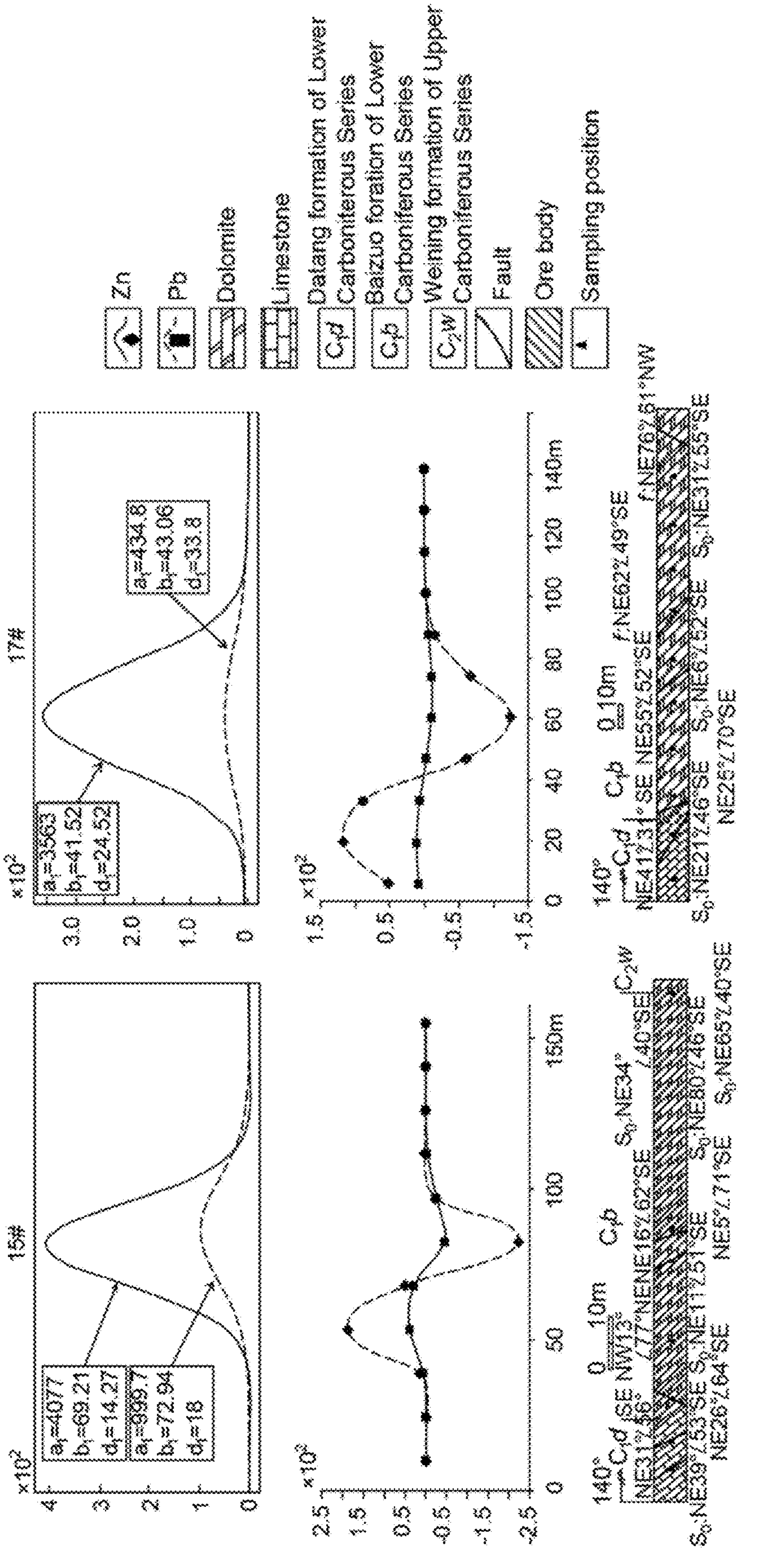
FIG. 2 is cross-section diagrams of 15 # and 17 # in a level of a certain deposit and distribution diagrams of contents of Pb and Zn elements in different veins, in which upper graphs shows fitting curve diagrams of Pb and Zn elements, middle graphs show first-order derivative scatter diagrams of a fitting curve versus the distance, and lower graphs shows measured cross-section diagrams.
Figure 3:
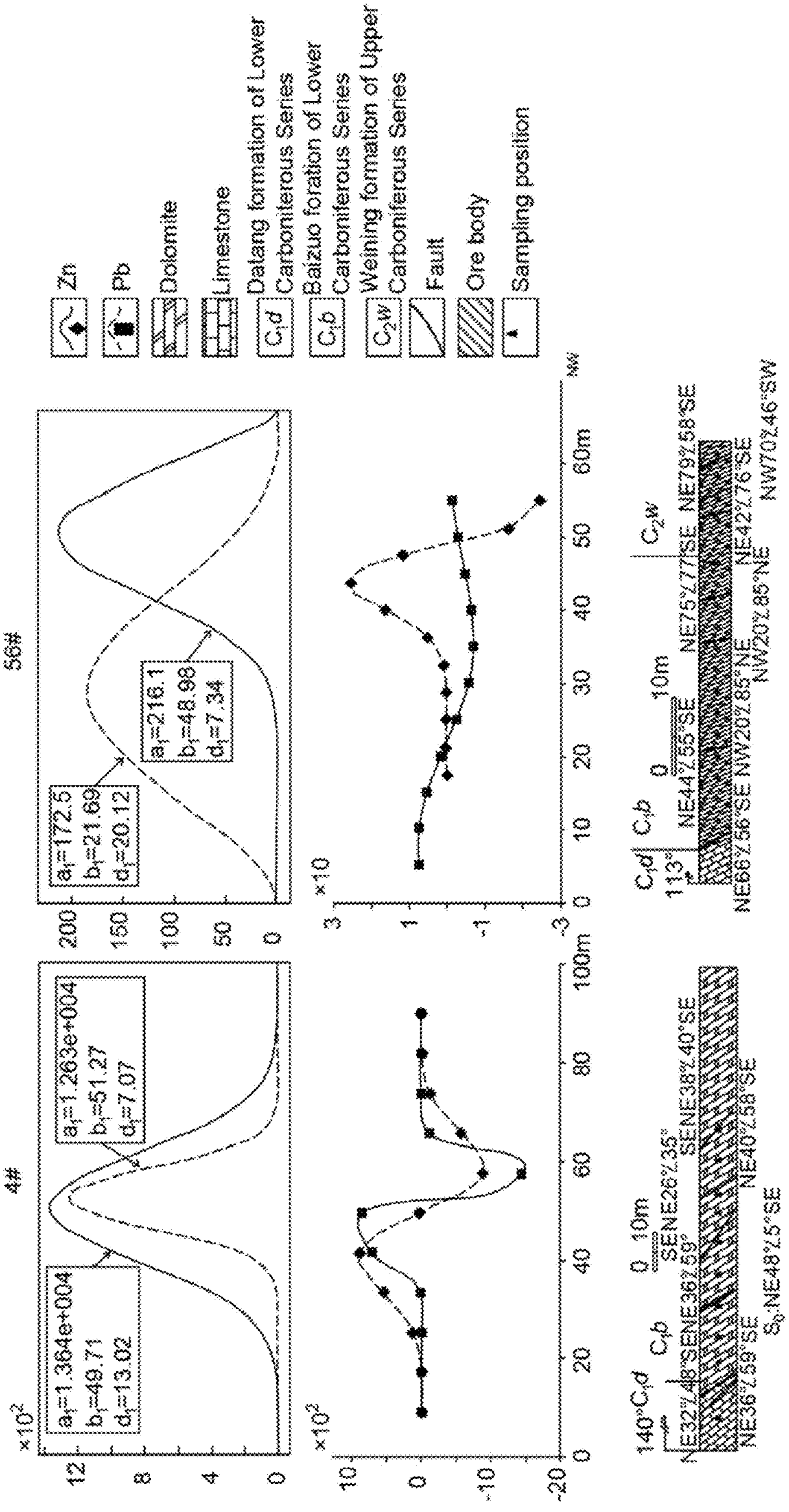
FIG. 3 is cross-section diagrams of 4 # and 56 # in a level of a certain deposit and distribution diagrams of content of Pb and Zn elements in different veins, in which upper graphs show fitting curve diagrams of Pb and Zn elements, middle graphs show first-order derivative scatter diagrams of a fitting curve versus the distance, and lower graphs show measured cross-section diagrams.

The specific implementation process of using the method of the present disclosure is as follows:

1. Measurement of a Metallogenic Structure Cross-Section and Systematic Collection of Samples (1) based on the ore field geomechanics theory and method, the structures in different directions in the vein tunnels of 4 #, 15 #, 17 #and 56 #of the level of the deep lower part of the mine area are finely analyzed. It is recognized that in the metallogenic epoch, the fracture in the northeast direction has left-lateral compression-shear, the fracture in the north-northwest direction has left-lateral shear-compression, the fracture in the near east-west direction has right-lateral shear, and the fracture in the northwest direction has torsional-shear. After mineralization, the near north-south fracture cuts through the structure in the metallogenic epoch. The left-lateral compression-shear fracture zone in the northeast direction directly controls the distribution of ore bodies in the interlayer compression-shear fracture zone in the northeast direction and its adjacent hydrothermal alteration zone, and makes a 1:500 scale structural cross-section (FIGS. 2 and 3).

(2) the ore-bearing structures and mineralized alteration points in different veins are determined, the mineralized altered rock samples are collected at a point distance of about 5-10 m according to the exposure of the ore-bearing fracture zone and mineralized altered rocks, and samples are intensively collected at places with strong mineralized alteration, in which the sampling length is 0.5-2 m. The collected samples are labelled on the structural cross-sections (FIGS. 2 and 3). The rocks and minerals are identified using a microscope, and the types of structural rocks and mineralized altered rocks are determined, which mainly include strong iron dolomite-pyritization-silicification pinhole coarse-grained dolomite, strong dolomite-calcitization coarse-grained dolomite, strong dolomite-calcitization medium-coarse-grained dolomite containing limestone dissolution breccia and calcitization-dolomite fine-grained limestone, as well as lead-zinc mineralized dolomite cataclasts, porphyries and reticulate and massive lead-zinc ores.

2. Sample Processing and Multi-Element Quantitative Analysis (1) In the pollution-free condition, the collected samples are processed and reduced to 200 meshes, and are classified into final samples and accessory samples; wherein the final samples are analyzed in the testing centre with national first-class qualification certification, and the accessory samples are used as a backup for inspection or retest.

(2) Multi-element quantitative analysis: a chemical method is used to analyze the samples with strong mineralization or below the cut-off grade, and the ICP-MS method is used to analyze the samples without strong mineralization. The contents of 45 elements such as Pb and Zn in the samples is quantitatively analyzed. Cipher samples or parallel samples are measured according to 3% of the total number of samples to test the accuracy of data. The average error is less than 5%. The testing method and the instrument precision both meet the analysis requirements. Elements satisfying normal or lognormal distribution are selected.

3. Mathematical Model Construction of Multi-Element Contents and Characteristic Element Combination Anomaly (1) According to the characteristics of the normal distribution in a cross-section, of lead-zinc metallogenic element content in different cross-sections, it is found that the boundary of the high-value area and the boundary of the low-value area of the ore-bearing cross-section are distinct, and the variation coefficient is relatively high, showing the characteristics of sudden increase and decrease, which is consistent with the geological fact that the boundary of the ore body and boundary of the ore-bearing surrounding rock are distinct.

Figure 4:
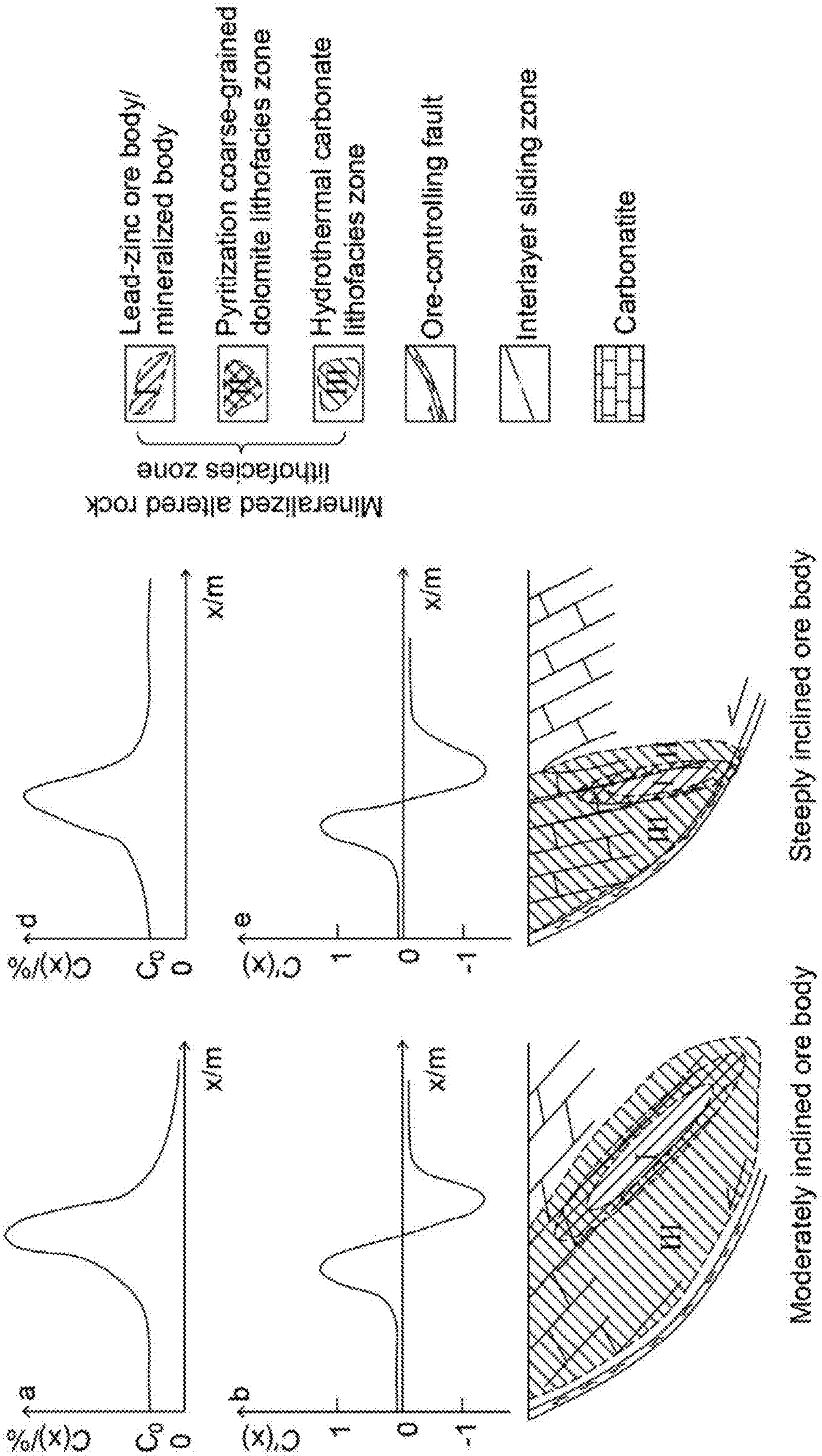
FIG. 4 is a diagram of metallogenic element distribution and an occurrence discrimination model of different inclined ore bodies of hydrothermal deposits.

(2) Based on the above functions, the variation trend of metallogenic elements is nearly the same through the functions of the characteristic element combination anomaly and the derivative function reflecting the occurrence of the deep concealed ore body. The element content c(x) has the following relationship with the spatial position x of interlayer fractures. The mathematical model objectively reflects the distribution characteristics of metallogenic elements (FIG. 4):

$$c(x) = a_1 \times e^{-((x-b_1x)/d_1)^2}.$$

Figure 5:
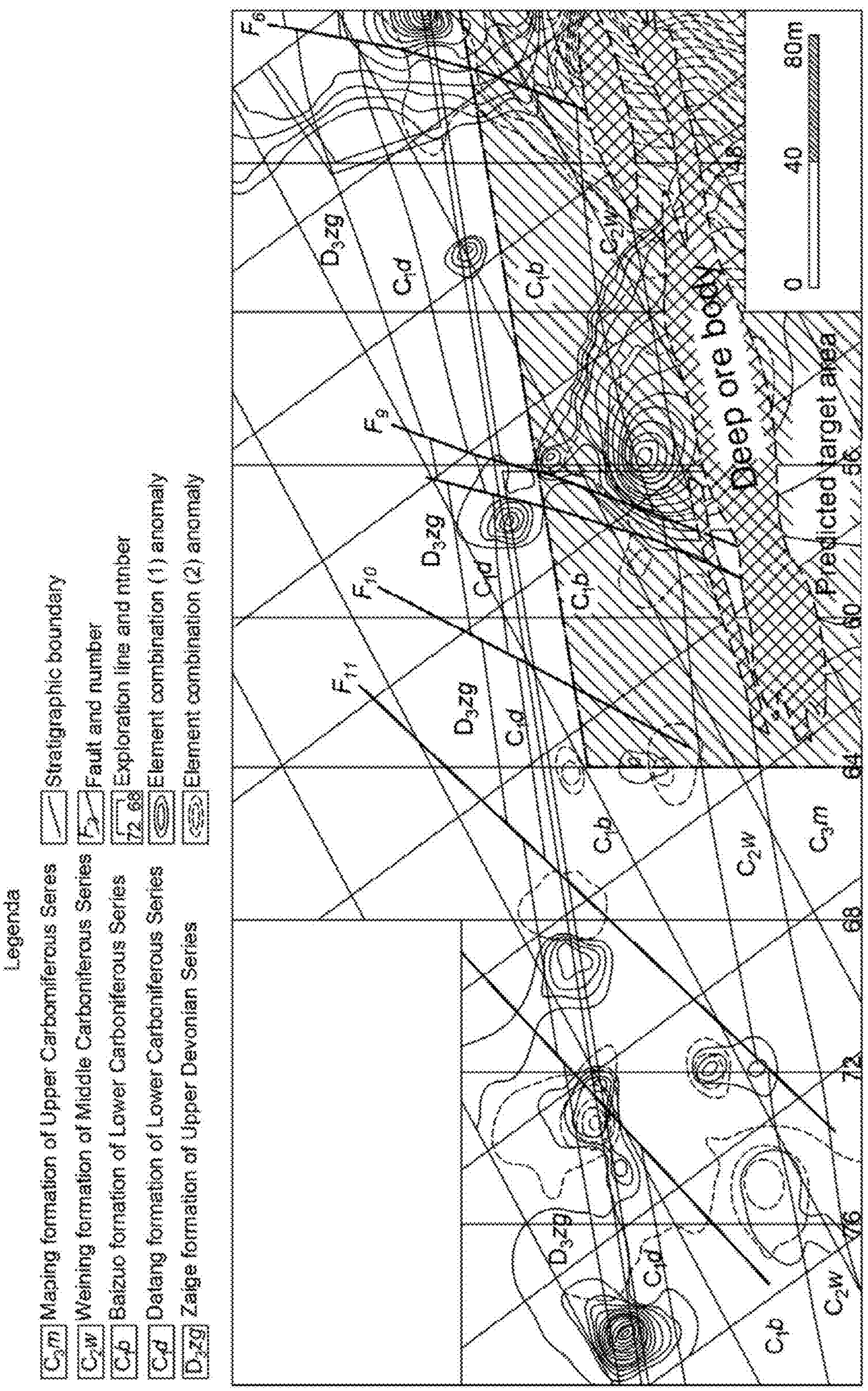
FIG. 5 is a diagram of distribution of characteristic element combination anomaly in a level of a certain deposit.

4. Determination of the Occurrence of the Deep Concealed Ore Body (1) If the combination anomaly of elements such as lead, zinc and so on $-0.03<F'(x)<-0.02$ (FIG. 5), it indicates that the dip direction of the concealed plate-shaped blind ore body is consistent with the abnormal divergence direction, that is, the dip direction of the deep concealed ore body is SE (southeast) direction, and the dip angle is relatively gentle.

(2) Because the characteristic element combination anomaly in the level of the lowermost part of the deep part is located in the left side of the characteristic element combination anomaly of the level of the upper part of the shallow part and the level of the uppermost part, it indicates that the deep blind ore body in the pitch direction to the left, that is, the SW (southwest) direction.

Embodiment 2: Determination of Occurrence of a Deep Concealed Plate-Shaped Ore Body in the Peripheral Exploration Area of a Germanium-Rich Lead-Zinc Deposit Although a lot of geological work has been carried out in the exploration area around a mine, little progress has been made in the deep prospecting, and only some small vein-like ore bodies have been discovered in the early stage. Hydrothermal alterations such as dolomite, pyritization, calcitization and silicification are developed in the Devonian and Carboniferous coarse-grained dolomite in the exploration area, which are obviously controlled by the left-lateral compression-shear structure. In particular, the dip angle of the deep ore body changes greatly on the cross-section, and the phenomenon of reverse dip is prominent. Although a geophysical prospecting method such as the Transient Electromagnetic Method (TEM) and the IP (Induced polarization method) is used, the inference and interpretation of resistivity and high polarizability anomalies obtained by these methods have strong multi-solutions, and water-bearing fractures, coal-bearing strata, surface high-voltage lines and underground track facilities in mines can result in anomalies similar to those of the ore body, so that it is difficult to distinguish whether the abnormal distribution characteristics indicating the occurrence of the deep ore body are mine-induced anomalies or non-mine-induced anomalies. It is difficult for the interpretation of geochemical anomalies to determine the occurrence of the deep concealed ore body.

Figure 6:
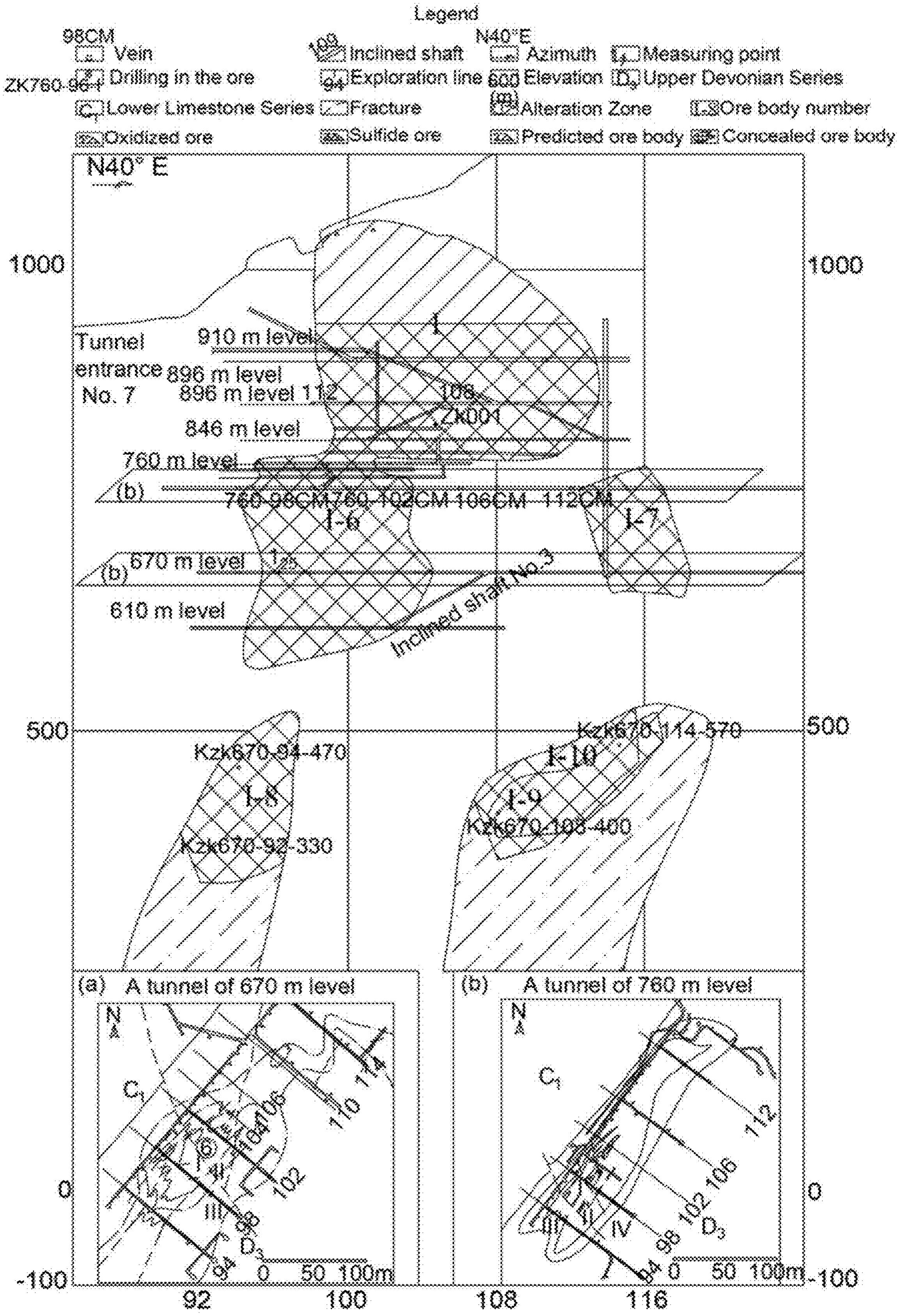
FIG. 6 is a vertical section projection of main ore body in a peripheral exploration area of a germanium-riched lead-zinc ore (upper graph), a level plane of a lower part (lower graph a) and a level plane of a lower part (lower graph b).
Figure 7:
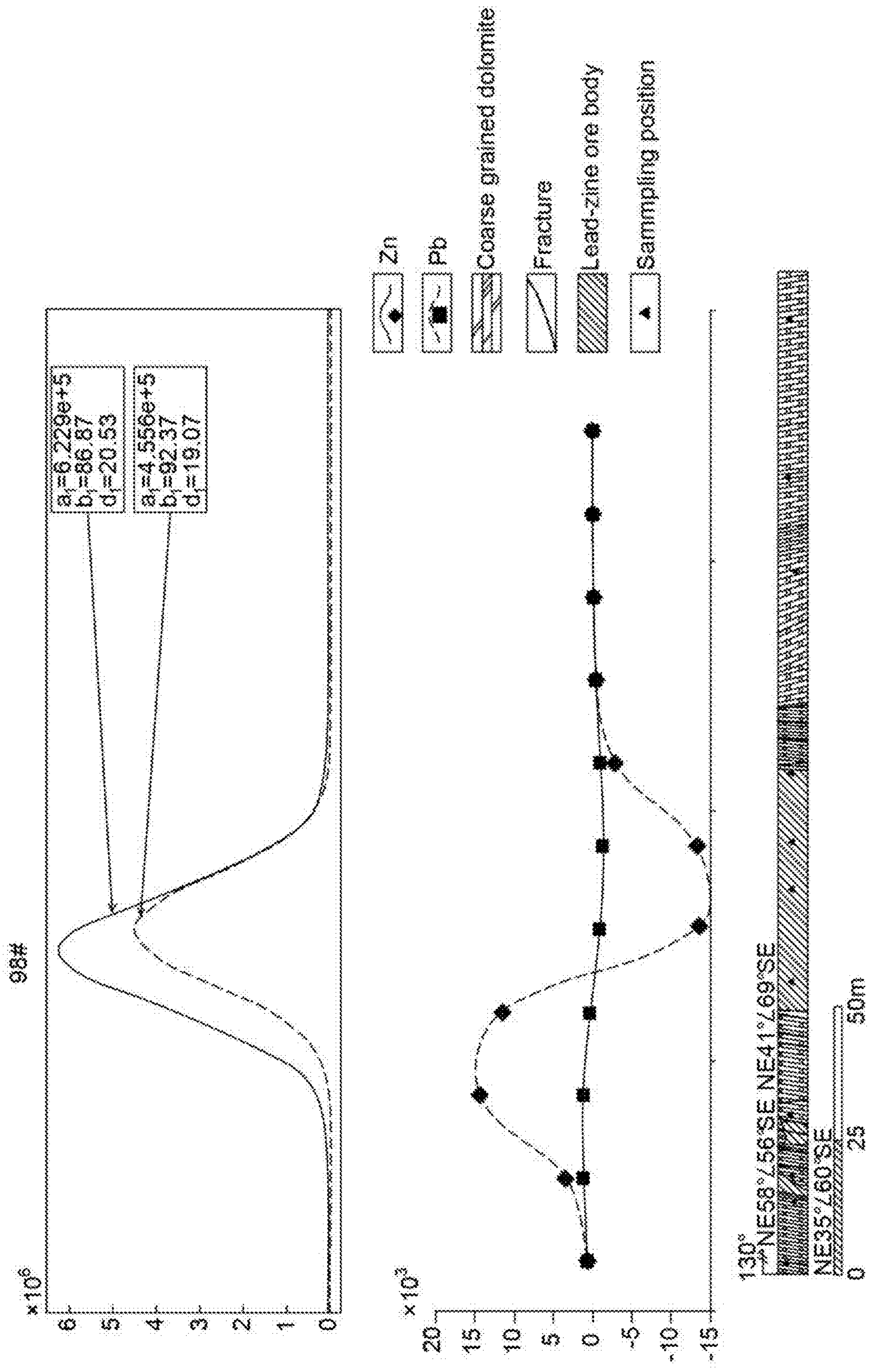
FIG. 7 is a diagram of distribution of Pb and Zn elements of 98 # vein in a level of a level of a lower part in an exploration area, in which an upper graph shows a fitting curve diagram of Pb and Zn elements, a middle graph shows a first-order derivative scatter diagram of a fitting curve versus the distance, and a lower graph shows a measured cross-section diagram.
Figure 8:
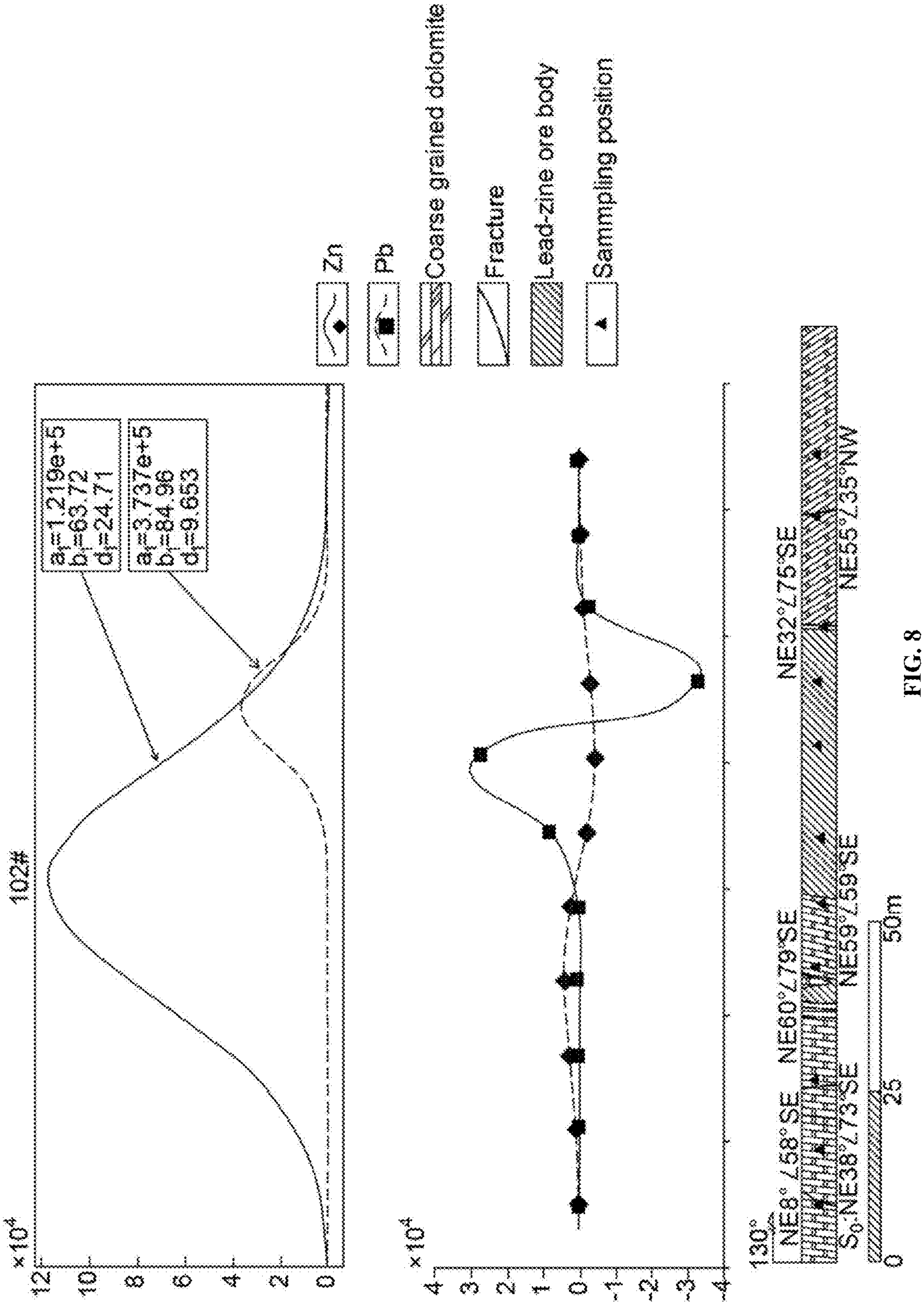
FIG. 8 is a diagram of distribution of Pb and Zn elements of 102 # vein in a level of a lower part in an exploration area, in which an upper graph shows a fitting curve diagram of Pb and Zn elements, a middle graph shows a first-order derivative scatter diagram of a fitting curve versus the distance, and a lower graph shows a measured cross-section diagram.
Figure 9:
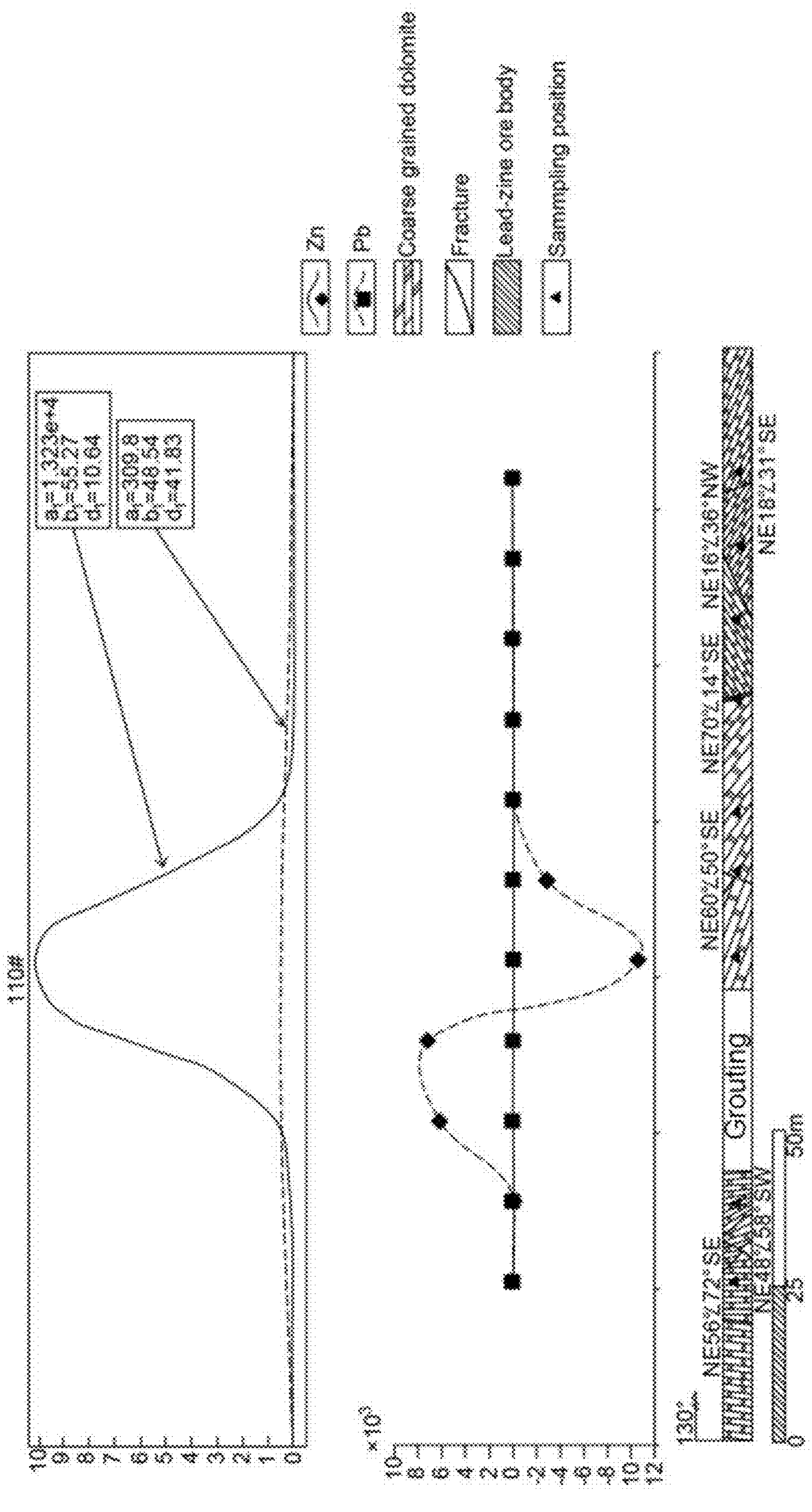
FIG. 9 is a diagram of distribution of Pb and Zn elements of 110 # vein in a level of a lower part in an exploration area, in which an upper graph shows a fitting curve diagram of Pb and Zn elements, a middle graph shows a first-order derivative scatter diagram of a fitting curve versus the distance, and a lower graph shows a measured cross-section diagram.
Figure 10:
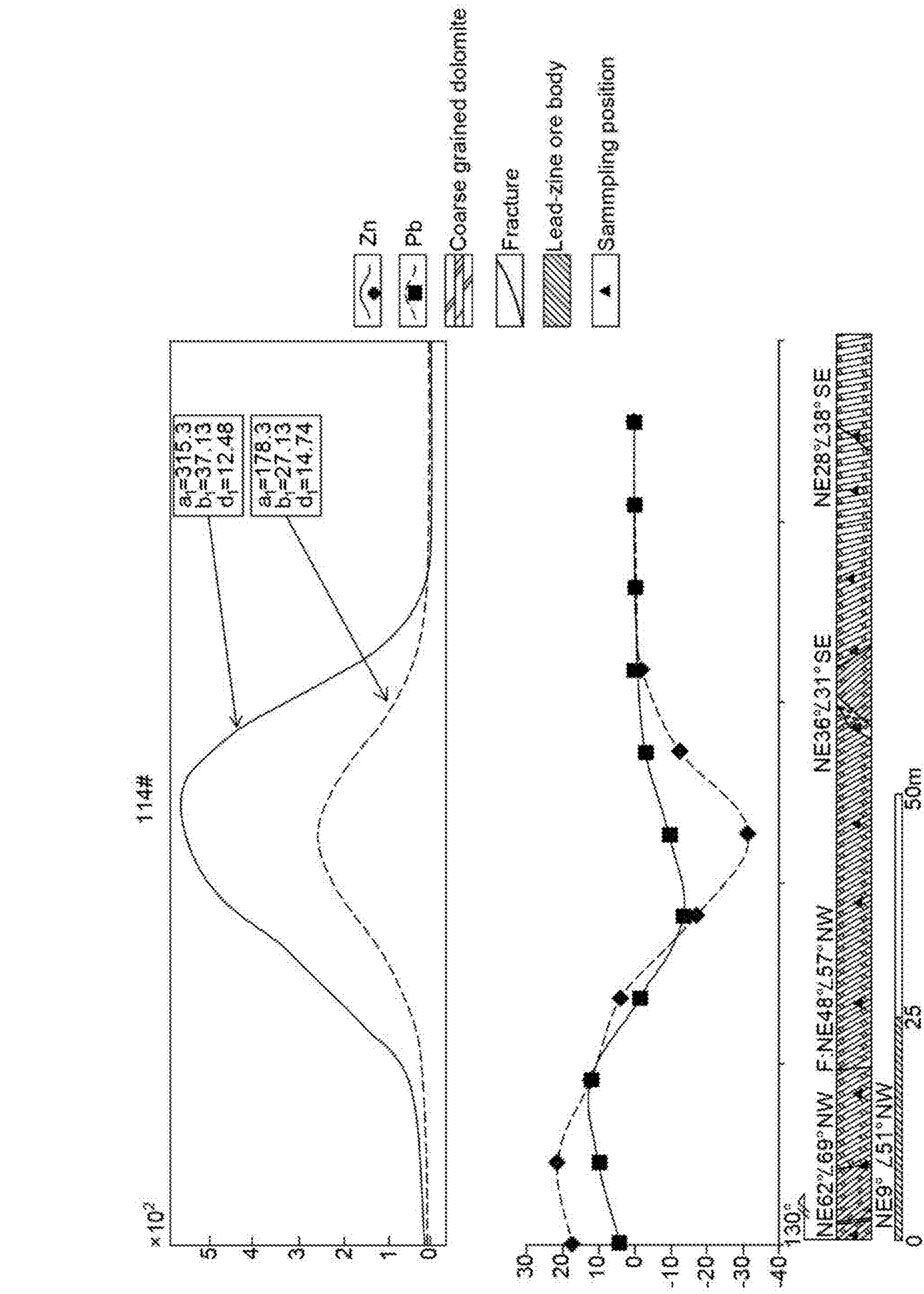
FIG. 10 is a diagram of distribution of Pb and Zn elements of 114 # vein in a level of a lower part in an exploration area, in which an upper graph shows a fitting curve diagram of Pb and Zn elements, a middle graph shows a first-order derivative scatter diagram of a fitting curve versus the distance, and a lower graph shows a measured cross-section diagram.
Figure 11:
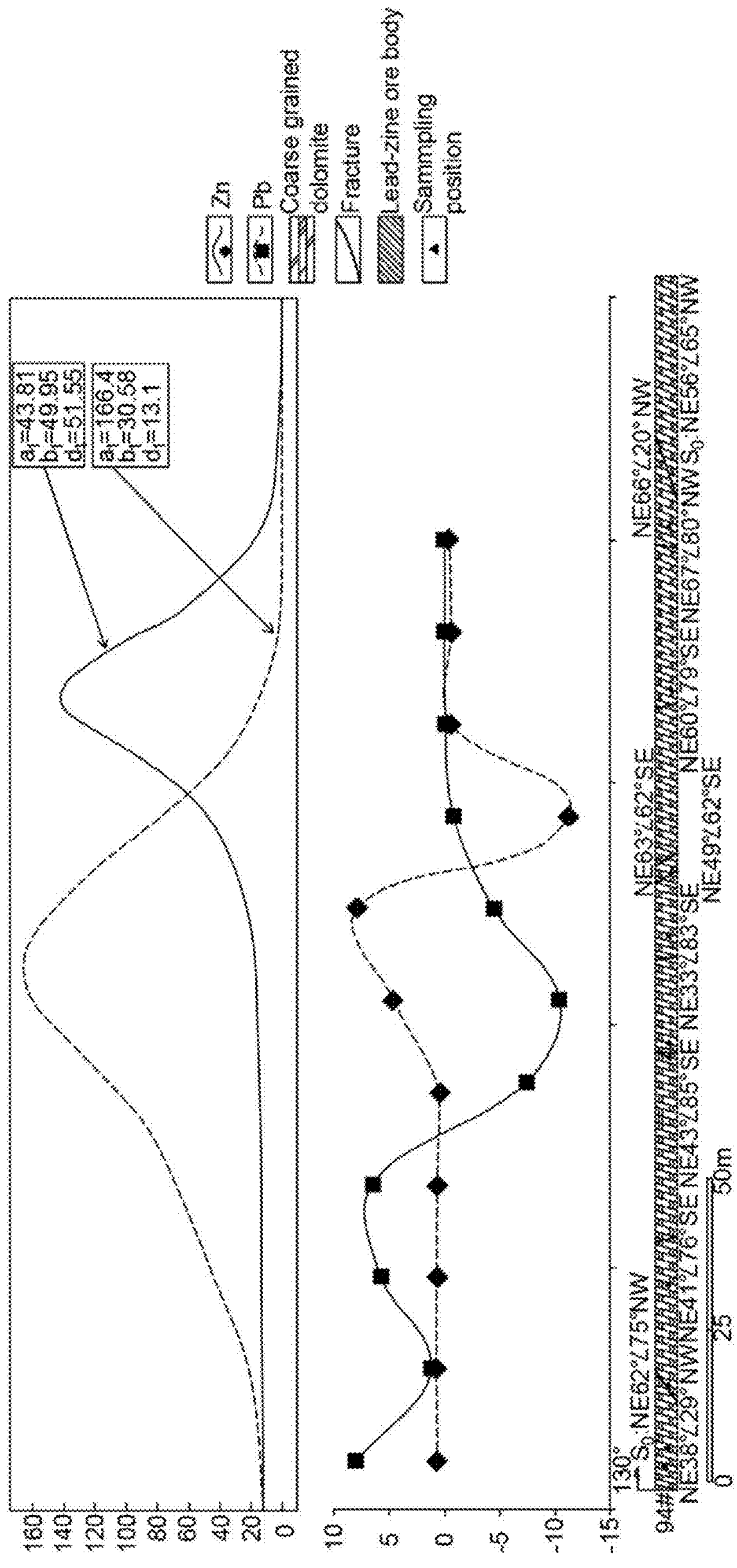
FIG. 11 is a diagram of distribution of Pb and Zn elements of 94 # vein in a level of an upper part in an exploration area, in which an upper graph shows a fitting curve diagram of Pb and Zn elements, a middle graph shows a first-order derivative scatter diagram of a fitting curve versus the distance, and a lower graph shows a measured cross-section diagram.
Figure 12:
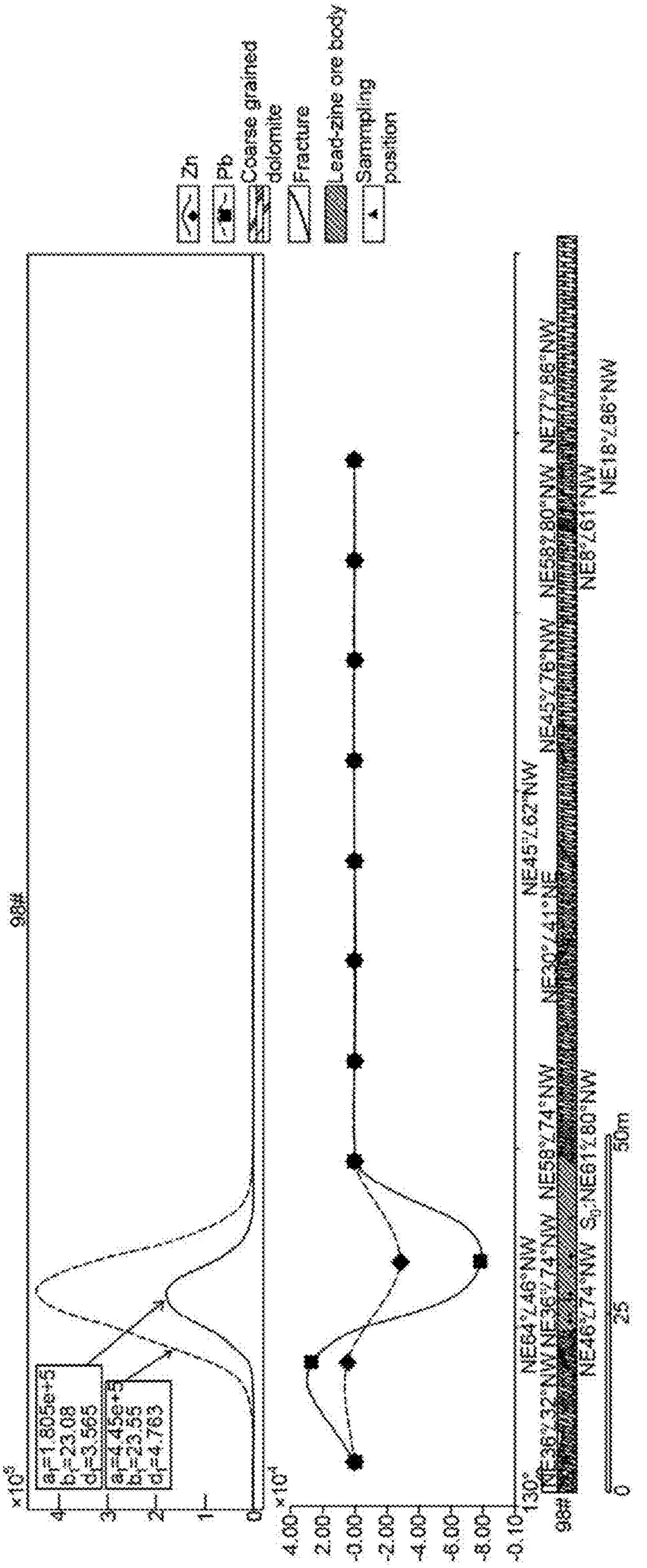
FIG. 12 is a diagram of distribution of Pb and Zn elements of 98 # vein in a level of an upper part in an exploration area, in which an upper graph shows a fitting curve diagram of Pb and Zn elements, a middle graph shows a first-order derivative scatter diagram of a fitting curve versus the distance, and a lower graph shows a measured cross-section diagram.
Figure 13:
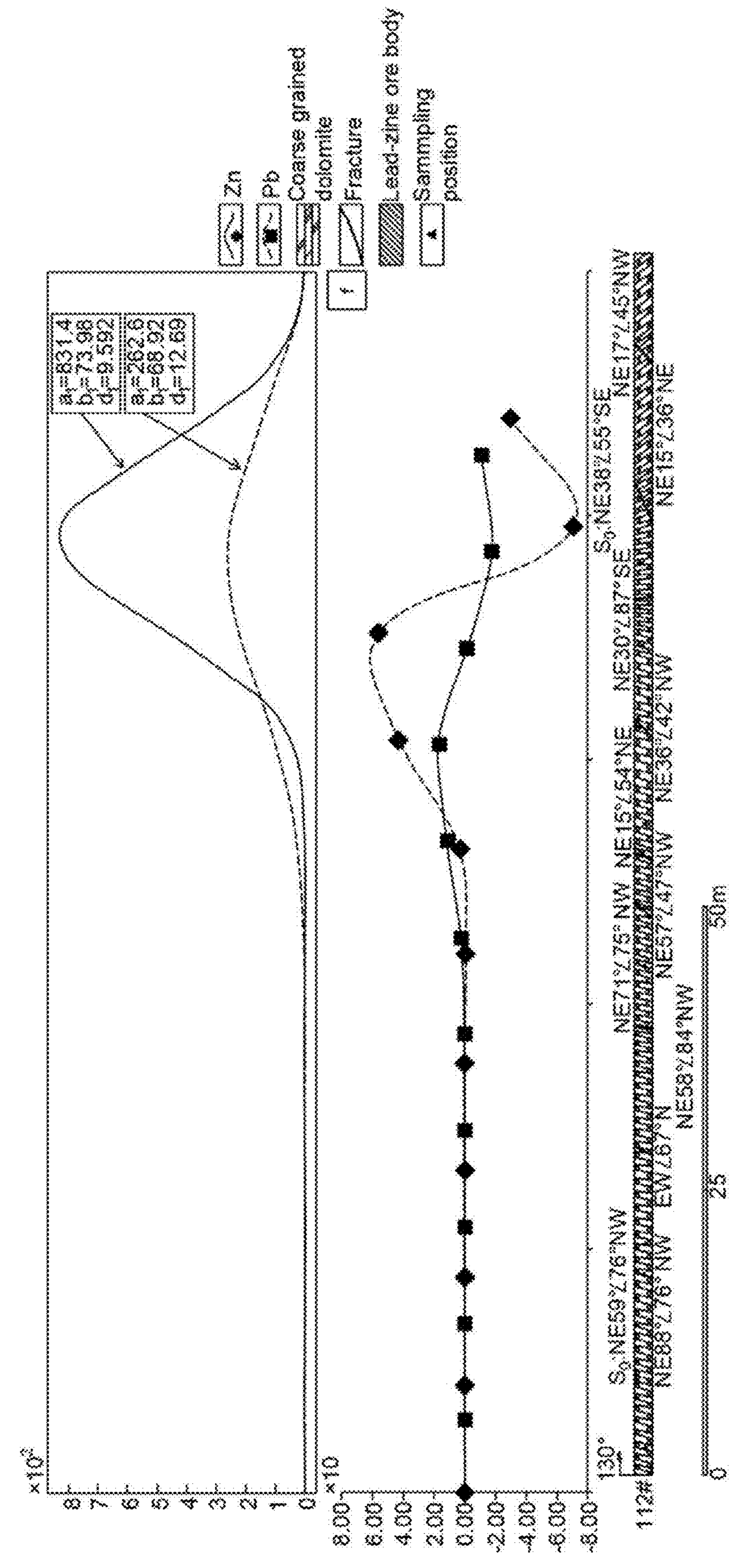
FIG. 13 is a diagram of distribution of Pb and Zn elements of 112 # vein in a level of an upper part in an exploration area, in which an upper graph shows a fitting curve diagram of Pb and Zn elements, a middle graph shows a first-order derivative scatter diagram of a fitting curve versus the distance, and a lower graph shows a measured cross-section diagram.

The deposit is a hydrothermal lead-zinc deposit obviously controlled by the combination of structures and rocks (FIG. 6), which lays a foundation for quantitative determination of the occurrence of the deep concealed plate-shaped ore body.

The specific implementation process of using the method of the present disclosure is as follows:

1. Measurement of a Metallogenic Structure Cross-Section and Systematic Collection of a Sample (1) based on an ore field geomechanics theory and a method thereof, the structures in different directions in the veins of 94 #, 98 #and 112 #of the level of the deep upper part and 94 #, 98 #, 102 #, 110 #and 114 #of the level of the deep lower part of the mine area are finely analyzed. It is recognized that in the metallogenic epoch, the fracture in the northeast direction has left-lateral compression-shear, the fracture in the north-northwest direction has left-lateral shear-torsion, and the fracture in the near north-south direction has left-lateral shear. The left-lateral compression-shear fracture zone in the northeast direction and NE (northeast)-direction compound overturned anticline directly control the distribution of ore bodies in the oblique strike-slip fault-compound anticline structural zone of the thermal solution brecciated dolomite alteration variant, and makes a 1:500 scale structural cross-section (FIGS. 7 to 13).

(2) the ore-bearing structures and mineralized alteration points in different veins are determined, the mineralized altered rock samples are collected at a point distance of about 5-10 m according to the ore-bearing fracture zone and the exposure of mineralized altered rocks, and samples are intensively collected at places with strong mineralized alteration, in which the sampling length is 0.5-2 m. The collected samples are labelled on the structural cross-section (FIGS. 7 to 13). The rocks and minerals are identified using a microscope, and the types of structural rocks and mineralized altered rocks are determined. From the center of the ore body to the surrounding rocks, the zoning law of mineralized altered rocks is as follows: lead-zinc silicified zone (I)→pyritized zone (II)→pyritized+dolomitized+calcified zone (III)→beige medium-coarse grained dolomitized zone (IV), in which the III zone is divided into three sub-zones: pyritized+dedolomitized macrocrystalline limestone (III-1), pyritized+weak marbling coarse-grained muddy dolomite (III-2), and pyritized+dolomitized+calcified (III-3).

2. Sample Processing and Multi-Element Quantitative Analysis (1) In the pollution-free condition, the collected samples are processed and reduced to 200 meshes, and are classified into final samples and accessory samples; wherein the multi-element contents of the final samples are analyzed in the testing centre with national first-class qualification certification.

(2) Multi-element quantitative analysis: a chemical method is used to analyze the samples with strong mineralization or below the cut-off grade, and the ICP-MS method is used to analyze the samples without strong mineralization. The contents of 45 elements such as Pb and Zn in the samples are quantitatively analyzed. Cipher samples or parallel samples are measured according to 3% of the total number of samples to test the accuracy of data. The average error is less than 5%. The testing method and the instrument precision both meet the analysis requirements. Elements satisfying normal or lognormal distribution are selected after being checked.

3. Mathematical Model Construction of Multi-Element Contents and Characteristic Element Combination Anomaly (1) According to the characteristics of the normal distribution in a cross-section, of lead-zinc metallogenic element content in different cross-sections, the mathematical expression of the geological point length x as an independent variable and element content c as a function is constructed. It is found that the boundary of the high-value area and the boundary of the low-value area of the ore-bearing cross-section are distinct, and the variation coefficient is relatively high, showing the characteristics of sudden increase and decrease, which is consistent with the geological fact that the boundary of the ore body and boundary of the ore-bearing surrounding rock are distinct.

(2) Based on the above functions, the variation trend of metallogenic elements is nearly the same through the function of the characteristic element combination anomaly and the derivative function reflecting the occurrence of the deep concealed ore body. The content c (x) has the following relationship with the spatial position x of interlayer fractures. The mathematical model objectively reflects the distribution characteristics of metallogenic elements: $c(x)=a_1\times e^{-((x-b_1x)/d_1)^2}$.

Figure 14:
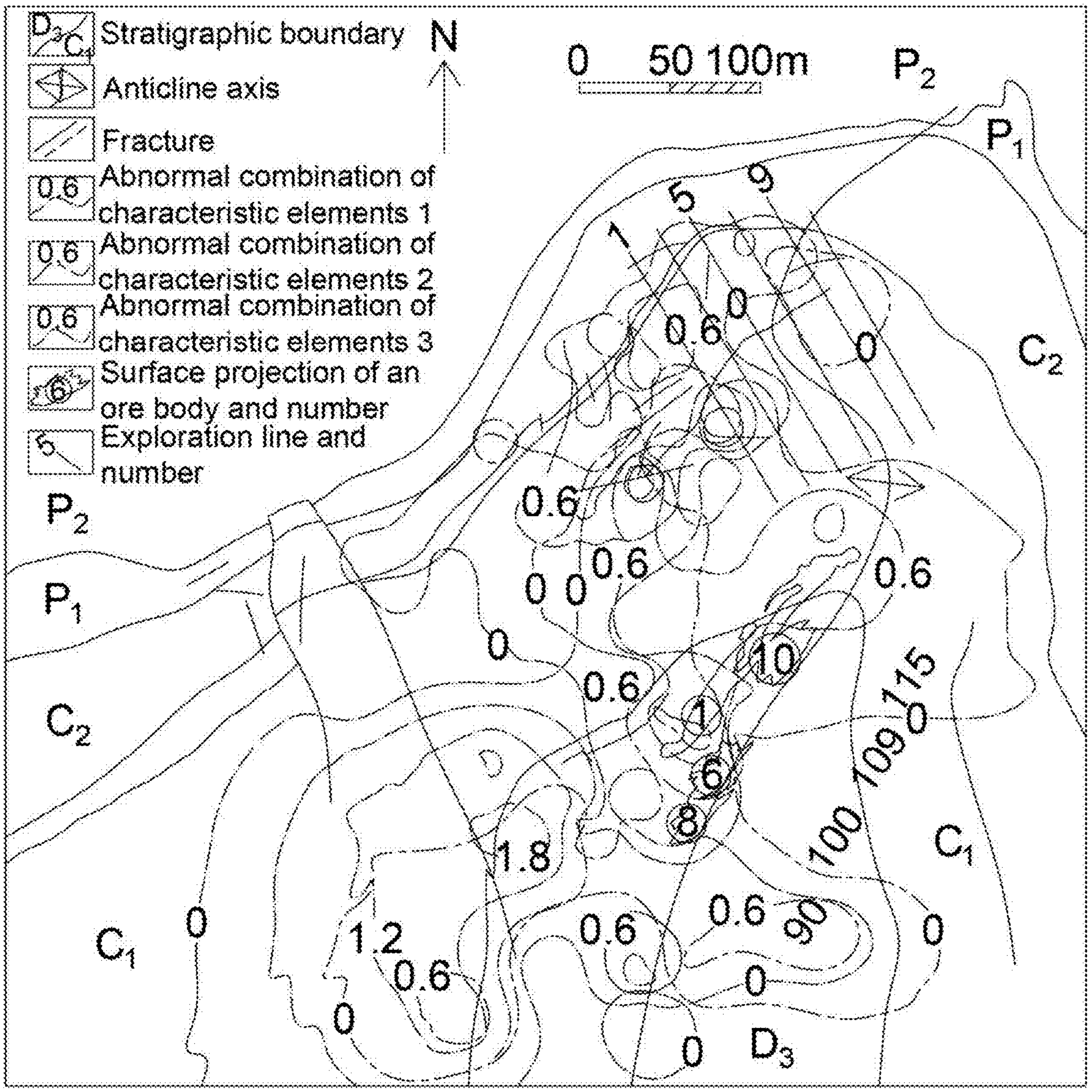
FIG. 14 is a diagram of distribution of characteristic element combination anomalies in a level of an upper part in an exploration area.

4. Existence of the Deep Concealed Ore Body and Determination of the Occurrence Thereof (1) If the combination anomaly of elements such as lead, zinc and so on F'(x)=(−0.006 to −0.01)<0 (FIG. 14), it indicates that the dip direction of the concealed ore body is consistent with the abnormal divergence direction, that is, the dip direction of the deep concealed ore body is SE (southeast) direction, and the dip angle of the concealed ore body is relatively steep.

(2) Because the characteristic element combination anomaly in the level of the deep part is located in the left side of the characteristic element combination anomaly in the level of the shallow part, it indicates that the deep blind ore body in the pitch direction to the left, that is, the SW (southwest) direction.

In embodiment 1 and embodiment 2 above, after determining occurrence, a target area is determined based on the determined occurrence of the deep concealed plate-shaped blind ore body, drilling holes are performed in the target area by a drilling rig, and a real occurrence of the deep concealed plate-shaped blind ore body below the target area is determined by ore body obtained from the drilling holes. After determining the real occurrence of the deep concealed plate-shaped blind ore body, ore body mining equipment is used to mine the deep concealed plate-shaped blind ore body under the target area according to the real occurrence.

What is claimed is:

1. A method for predicting occurrence of a deep concealed plate-shaped ore body of a hydrothermal deposit, comprising:

based on an ore field geomechanics theory and a method thereof, finely measuring and analyzing metallogenic structures in different levels and different veins or cross-sections in a deep tunnel of the hydrothermal deposit, and recognizing types of the metallogenic structures in a mine area to identify mineralized altered rocks distributed along the metallogenic structures and draw structural cross-section diagrams;

collecting samples of metallogenic faulted rocks or the mineralized altered rocks at a point distance of 5-20 m, and labeling the collected samples on a geological map;

classifying the collected samples into final samples and accessory samples, and analyzing contents of main metallogenic elements and trace elements related to mineralization of the final samples to determine whether a distribution of each element content conforms to a normal or lognormal distribution, and select elements satisfying the normal or lognormal distribution;

based on the element content that conforms to the normal or lognormal distribution in a measured cross-section, using factor analysis and cluster analysis methods to obtain characteristic element combination indicating deep mineralization information and characteristic element combination anomaly, analyzing a variation law of the characteristic element combination anomaly, and constructing a single element distribution model based on a sampling geological point position x of different cross-section as an independent variable and a characteristic element content $c_i$ as a function to reflect the lognormal distribution of the content of an element i in a cross-section;

$$c_i = f(x) = a_1 \times \exp\left(-\left((x - b_1 x)/d_1\right)^2\right)$$

wherein f(x) is the element content in unit of $10^{-6}$; x is a distance in unit of m; $a_1$, $b_1$ and $d_1$ are constants; and i is the element;

constructing a characteristic element combination anomaly model based on a sampling geological point position x of different cross-sections as an independent variable and a characteristic element combination anomaly $C_j$ as a function to reflect characteristics of the lognormal distribution of the characteristic element combination anomaly $C_i$ in a cross-section;

$$C_j = F(x) = A_1 \times \exp\left(-\left((x - B_1 x)/D_1\right)^2\right)$$

wherein F(x) is the characteristic element combination anomaly, which is a non-dimensional unit; x is a distance in unit of m; $A_1$, $B_1$ and $D_1$ are constants; j is a characteristic element combination indicating deep mineralization information;

obtaining a first-order derivative function reflecting a dip direction of the deep concealed plate-shaped ore body by a first-order derivative of the characteristic element combination anomaly model:

$$\frac{dC}{dx} = F'(x) = \frac{-2(1 - B_1)^2 x}{D_1^2} \times A_1 \times e^{|-[(1-B_1)x/D_1)]^2|};$$

determining the occurrence of the deep concealed plate-shaped ore body based on the first-order derivative function, comprising:

determining the dip direction and a dip angle of the deep concealed plate-shaped ore body;

wherein, if F'(x)<0, it indicates that the dip direction of the concealed plate-shaped ore body is consistent with an abnormal divergence direction;

if F'(x)>0, it indicates that the dip direction of the concealed plate-shaped ore body is opposite to the abnormal divergence direction;

if F'(x)=(−0.01, 0.01) but ≠0, it indicates that the dip angle of the concealed plate-shaped blind ore body is steep; and if |F'(x)|>0.01, it indicates that the dip angle of the concealed plate-shaped ore body is gentle;

determining strike of the deep concealed plate-shaped ore body;

wherein if F'(x)=0 and is distributed linearly, the strike of the deep concealed plate-shaped ore body is consistent with a linear direction;

determining a pitch direction of the deep concealed plate-shaped ore body;

wherein an abnormal drift direction of different elevation planes indicates the pitch direction of the concealed plate-shaped ore body;

if the characteristic element combination anomaly in a deep plane is located to a left of the characteristic element combination anomaly in a shallow plane, it indicates that the concealed plate-shaped ore body is in the pitch direction to a left;

if the characteristic element combination anomaly in the deep plane is located to a right of the characteristic element combination anomaly in the shallow plane, it indicates that the concealed plate-shaped ore body is in the pitch direction to a right;

if the characteristic element combination anomaly in the deep plane and the characteristic element combination anomaly in the shallow plane are in a same position on planes, it indicates that the concealed plate-shaped ore body is not in the pitch direction; and based on the determined occurrence of the deep concealed plate-shaped ore body, prospecting and exploring the deep concealed plate-shaped ore body of the hydrothermal deposit.

2. The method for predicting the occurrence of the deep concealed plate-shaped ore body of the hydrothermal deposit according to claim 1, wherein a scale of 1:200 to 1:10000 is used.

* * * * *